(12) United States Patent
Doucet et al.

(10) Patent No.: US 8,986,718 B2
(45) Date of Patent: Mar. 24, 2015

(54) COMPOSITION WITH IMPROVED TANNING EFFECT

(75) Inventors: Olivier Doucet, Roquebrune Cap Martin (FR); Muriel Pujos, West New York, NJ (US); Cecile Robert, Nice (FR); Dorothee Bernini, Monaco (MC)

(73) Assignee: Coty Germany GmbH, Mainz (DE)

( * ) Notice: Subject to any disclaimer, the term of this patent is extended or adjusted under 35 U.S.C. 154(b) by 0 days.

(21) Appl. No.: 13/435,610

(22) Filed: Mar. 30, 2012

(65) Prior Publication Data

US 2012/0251602 A1 Oct. 4, 2012

(30) Foreign Application Priority Data

Mar. 31, 2011 (EP) ..................................... 11160592

(51) Int. Cl.
*A61K 8/97* (2006.01)
*A61Q 17/04* (2006.01)
*A61Q 19/04* (2006.01)
*A61K 8/58* (2006.01)
*A61K 8/44* (2006.01)
*A61K 8/49* (2006.01)
*A61K 8/92* (2006.01)
*A61Q 19/00* (2006.01)

(52) U.S. Cl.
CPC . *A61K 8/585* (2013.01); *A61K 8/44* (2013.01); *A61K 8/4953* (2013.01); *A61K 8/922* (2013.01); *A61K 8/97* (2013.01); *A61Q 19/04* (2013.01); *A61Q 19/004* (2013.01)
USPC ............................................ 424/401; 424/59

(58) Field of Classification Search
USPC .................................................. 424/401, 59
See application file for complete search history.

(56) References Cited

U.S. PATENT DOCUMENTS 5,037,803 A * 8/1991 Gueyne et al. ................ 514/16.5
7,731,942 B2 6/2010 Golz-Berner 2002/0025303 A1 * 2/2002 Fructus et al. ............. 424/78.03
2005/0271595 A1 * 12/2005 Brown .......................... 424/10.1
2009/0269375 A1 * 10/2009 Patnode ........................ 424/401
2009/0297466 A1 * 12/2009 Gutmann et al. ........... 424/70.12
2009/0311202 A1 * 12/2009 Golz-Berner et al. .......... 424/59
2010/0150853 A1 * 6/2010 Cassin et al. .................... 424/59
2010/0158833 A1 * 6/2010 Clemente et al. ............... 424/59

FOREIGN PATENT DOCUMENTS

| DE | 102004062170 B3 | 6/2006 | | |
|---|---|---|---|---|
| DE | 202008014069 U1 | 10/2009 | | |
| EP | 0380335 A2 | 8/1990 | | |
| FR | 2845285 A1 | 4/2004 | | |
| WO | WO-2010118880 | * | 10/2010 | ............... C07K 5/08 |

OTHER PUBLICATIONS

Stern, Essentilaity and toxicity in copper health risk assessment: overview, update and regulatory considerations, Journal of Toxicology and Environmental Health, Part A, 2010, vol. 73, p. 114-127.*
Happi, Sun care is back, 2006, pp. 1-23.*
Barel et al. 3rd Ed. Handbooks for cosmetic science and technology, Informa Healthcare, 2009, Chapter 31 and chapter 32.*
Database GNPD [Online] Mintel; "Tanning Preparation Milk Gradual Tan", Jul. 2010, pp. 1-4.
Zanatta et al., "Photoprotective potential of emulsions formulated with Buriti oil (*Maurita flexuosa*) against UV irradiation on keratinocytes and fibroblasts cell lines," Food and Chemical Toxicology 48, 2010 , pp. 70-75.
European Search Report dated Sep. 30, 2011 for EP Application No. 11160592.9 consisting of 7 pages.
Data Sheet for Lasilium® 2008.
International Cosmetic Ingredient Dictionary and Handbook, Twelfth Edition, 2008, vol. 2, INCI Name Monographs L-S, pp. 1390, 1581 and 2536.

* cited by examiner

*Primary Examiner* — Kevin S. Orwig
*Assistant Examiner* — Ping Cao
(74) *Attorney, Agent, or Firm* — Novak Druce Connolly Bove + Quigg LLP

(57) ABSTRACT

The invention refers to a composition with improved tanning effect in cosmetic and dermatological applications. The composition comprises Caffeine, Glycine, Hydrolyzed Citrus Aurantium Dulcis Fruit Extract, Sodium Lactate Methylsilanol, Mauritia Flexuosa Fruit Oil and usual cosmetic or dermatological auxiliaries. The composition shows a synergistic tanning effect.

10 Claims, No Drawings

COMPOSITION WITH IMPROVED TANNING EFFECT

CROSS-REFERENCE TO RELATED APPLICATIONS

This Application claims priority to European Patent Application No. 11160592.9, filed Mar. 31, 2011, the entirety of which is incorporated herein by reference.

The invention refers to a composition with improved tanning effect for human skin and the use of the composition in dermatological and cosmetic applications.

EP 380335 A2 describes sun tan accelerator compositions comprising a copper salt such as copper gluconate together with a xanthin such as caffeine or theophylline.

U.S. Pat. No. 7,731,942 B2 discloses a body modelling kit of three different products wherein the pre-product comprises, beside other things, also copper gluconate and caffeine. The secondary product after sun irradiation comprises, beside other things, also copper gluconate and optionally a hydrolyzed Citrus aurantium extract for more intensive tanning.

Object of the present invention is to develop a new composition with improved tanning effect and its cosmetic and dermatological use.

The invention also relates to a method for tanning human skin by applying to the concerned area the tanning composition as described below.

The tanning composition of the invention comprises Caffeine, Glycine, Hydrolyzed Citrus Aurantium Dulcis Fruit Extract, Sodium Lactate Methylsilanol and Mauritia Flexuosa Fruit Oil as well as dermatological or cosmetic auxiliaries. The composition can be prepared in any usual cosmetic and dermatological application forms such as emulsions, oils, gels etc.

In more detail the present invention refers to a tanning composition comprising 0.05 to 2.0% Caffeine,
0.01 to 1.0% Glycine,
0.001 to 0.2% Hydrolyzed Citrus Aurantium Dulcis Fruit Extract,
0.05 to 0.5% Sodium Lactate Methylsilanol and
0.05 to 3.0% Mauritia Flexuosa Fruit Oil,
and the difference to 100% usual dermatological or cosmetic auxiliaries,
all in weight % and related to the total weight of the composition.

The Hydrolyzed Citrus Aurantium Dulcis Fruit Extract is an extract prepared by extraction with water at temperatures of 20-35° C. A preferred amount of the extract in the composition is 0.01-0.05% by weight. A known product on the market is e.g. Biotanning®, Silab, Brive, France.

Caffeine is a solid white powder and is available on the market as a usual cosmetic raw material supplied e.g. as AEC Caffeine Powder® (A&E Connock), Coffeine (Merck KGaA), Caffeine naturelle Anhydre (Provital), or in a glycolic compound such as Lipocare® (Sederma). A preferred amount of Caffeine in the tanning composition is 0.1-1.2% by weight.

The Mauritia Flexuosa Fruit Oil is an oil which is obtained by cold pressing of the fruit pulp. Mauritia flexuosa is a very tall palm tree native of North Eastern South America and is extensively abundant in central Brazilian areas in the entire Amazon basin. The fruit contains carotenoids and fatty acids such as oleic acid and palmitic acid. A preferred amount in the tanning composition is 0.05-1.0% by weight, more preferably 0.05-0.6% by weight. Known products on the market are, Melscreen Buriti® (Chemyunion), Crodarom Buriti® (Chrodarom), Buriti Oil (Beraca Ingredients).

Sodium Lactate Methylsilanol is a silanol obtained by condensation of a synthetic derivative of silicon on lactic acid. The silicon derivative is obtained by synthesis, the lactic acid is obtained by fermentation from sugar. A known product on the market is Lasilium® (Exsymol SAM). A preferred amount of Sodium Lactate Methylsilanol in the composition is 0.05-0.25% by weight.

From the above-discussed state of the art a certain tanning effect was to be expected, but in any case together with copper gluconate. It was therefore completely surprising that the tanning effect was significantly enhanced up to a synergistic effect without the copper gluconate but in combination with another plant oil.

The synergistic effect of nearly 300% over the combination of EP 380335 is described in more detail in the comparison test.

In a second aspect the invention relates to the use of the described tanning composition in different cosmetic application forms. For such application forms the composition further comprises usual dermatological or cosmetic ingredients, e.g. antioxidants, radical scavengers, inorganic and organic sunscreens (UV filters), emulsifying agents, pigments, preservatives, gel formers, dyes, perfumes, stabilisers, film-forming agents, emollients, conditioning agents, moisturizing substances, chelating agents, SPF boosters, humectants, anti-inflammatory natural active agents, pH regulators etc.

Specially preferred are antioxidants, radical scavengers, UV filters, emulsifying agents, moisturizing substances, gel formers, SPF boosters, emollients, silicone oils, emulsion stabilisers, pH regulators, preservatives.

Additional dermatological or cosmetic auxiliaries which can be used in the composition include e.g. water, vitamins, enzymes, other plant extracts, polymers, enzymes, phospholipids, panthenol, allantoin, synthetic ethers and esters, fatty acids, monovalent and multivalent alcohols, silicones, minerals, further oils, especially plant oils and/or biotechnological extracts. Such biotechnological extracts are e.g. CLR Repair Complex or Yeast Complex B, both of CLR Chem. Lab. Dr. Kurt Richter GmbH, Berlin, Germany; or Stimulhyal, Primalhyal 50 or 300, all of SOLIANCE, Paris, France.

Specially preferred are water, vitamins, other plant extracts and mixtures of extracts, synthetic polymers, esters, ethers, fatty acids, monovalent and multivalent alcohols, silicones, silicates.

A preferred optional plant oil is Red Palm Oil which supports the tanning action, especially together with Bixa Orellana Seed Extract.

Another preferred optional ingredient is β-carotene which is usually present as micronised crystals dispersed in an oil such as corn oil and together with an antioxidative and stabilizing amount of α-Tocopherol.

The preferred Red Palm Oil (Elaeis Guineensis) comprises carotenoids, tocopherols and tocotrienols in a range of 400-1600 ppm. A preferred amount of this product (e.g. Cegesoft® GPO, Cognis) is 0.05-1.5% by weight, more preferably 0.05-0.5% by weight.

The preferred auxiliary Bixa Orellana Seed Extract is an extract prepared by extractions of the seed with Caprylic/Capric Triglyceride and comprises high contents of δ- and γ-tocotrienol (5-8% by weight of the extract concentrate). The extract is a product available on the market with the INCI name of Caprylic/Capric Triglyceride & Bixa Orellana Seed Extract, as products e.g. Rocou HPG Titrated® Alban Muller), Phytessence Urucum® (Crodarom), Paprika P-AC-3® (Heidelberger). This product shows also antioxidative effects due to its high content especially of δ-tocotrienol. Furthermore it enhances the tanning effect. A preferred amount of Bixa Orellana Seed is 0.005-0.5 by weight, preferably 0.01-0.2, especially preferred 0.01-0.15% by weight.

The antioxidants which may be contained in the tanning composition of the invention include e.g. vitamins such as vitamin C and derivatives thereof, for example, ascorbic acetate, phosphate, and palmitate; folic acid and derivatives thereof; vitamin E and derivatives thereof, such as tocopheryl acetate; flavones or flavonoids; furthermore amino acids, such as histidine, tyrosine, tryptophan, and derivatives thereof; imidazole such as cis- or trans-urocaninic acid and their derivatives; peptides such as D,L-carnosine, D-carnosine, L-carnosine and their derivatives; hyaluronic acid; lycopene; uric acid and derivatives thereof; α-hydroxy acids such as citric acid, lactic acid, malic acid; α-hydroxy fatty acids such as palmitic acid, phytic acid, lactoferrin; mannose and their derivatives; liponic acid and their derivatives such as dihydro liponic acid; ferulic acid and their derivatives; thiols such as glutathione, cysteine and cystine.

The addition of hyaluronic acid and/or vitamin E is especially preferred.

A further preferred radical scavenger which may be comprised by the tanning composition of the invention is a mixture of the following plant extracts: Angelica Archangelica Root Extract, Camellia Sinensis Leaf Extract, Pongamia Pinnata Seed Extract, Coffea Arabica Seed Extract. These four extracts may be formulated as an alcoholic preparation which comprises 0.2 wt % of each plant extract and about 99 wt % alcohol, as an encapsulated liposomale preparation which comprises 2 wt % of each plant extract, 5 to 10% alcohol and 3 to 7 wt % lecithin, or as an non-encapsulated oily preparation which comprises about 90 wt % Caprylic/Capric Triclyceride, about 0.9 to 1 wt % of each Camellia Simensis Leaf Extract and Coffea Arabica Seed Extract and about 0.1 wt % of each Angelica Archangelica Root extract and Pongamia pinnate Seed Extract. These preparations may additionally contain Citrus Auranthium (Bitter Orange) Peel Extract, preferably 0.1 wt %. All here given percentages relate to the preparation of the four plant extracts. This preparation may be contained in the composition of the invention from 0.1 to 1 wt %, related to the composition of the invention. All mentioned extracts are known products and are commercially available on the market. According to the invention the encapsulated liposomale preparation is especially preferred.

The tanning composition of the invention can be used in different cosmetic products such as lotions, oils, creams, gels, masks, balms, powders, tan glows, pre-sun products, sun products, after-sun products, self-tans, make-ups, compact powders, photoprotecting products, sprays.

Emulsion products include multiple emulsions, micro emulsions and nano emulsions in the form of W/O, O/W, W/Si, Si/W, W/O/W, O/W/O, O/W/Si and W/Si/W emulsions (O=Oil, W=Water, Si=Silicone). Other products such as anhydrous systems like Si/O are also included.

Pre-sun products are e.g. pre-sun gels, pre-sun lotions, pre-sun creams or pre-sun oils. Sun products are gels, creams, lotions, oils or sprays with different Sun Protection Factors (SPF) in the range from SPF 6 to SPF 50+, e.g. SPF 6, SPF 10, SPF 15, SPF 20, SPF 25, SPF 30, SPF 50 and SPF 50+. The different SPFs are dependent on the kind and amount of UV filter substances.

Suitable cosmetic gel-forming agents for the preparation of a gel are carbomer, xanthan gum, carrageenan, acacia gum, guar gum, agar-agar, alginates and tyloses, magnesium aluminium silicate, carboxymethyl cellulose, hydroxyethyl cellulose, quaternized cellulose, quaternized guar, certain polyacrylates, such as acrylates/C10-30 alkyl acrylate crosspolymer, polyvinyl alcohol, polyvinylpyrrolidone.

Specially preferred are xanthan gum, Carbomer, Ammonium Acryloyldimethyltaurate/VP Copolymer Ammonium Acryloyldimethyltaurate/Beheneth-25 Methacrylate Crosspolymer Acrylates/C12-22 Alkyl Methacrylate Copolymer, Magnesium Aluminium Silicate, Sodium Acrylate/Sodium Acryloyldimethyl Taurate Copolymer, Hydroxyethyl Acrylate/Sodium Acryloyl Dimethyl Taurate Copolymer, Polyester-5 and Acrylates/Vinyl Neodeconoate Crosspolymer, Sodium Polyacrylate, Polyacrylamide/C13-14 Isoparaffin/Laureth 7.

For the preparation of sun products it is moreover advantageous to use in a composition together with the inventive tanning ingredients corresponding water and/or oil soluble UVA or UVB filters or both. Advantageous oil-soluble UVB filters include 4-amino benzoic acid derivatives such as 4-(dimethylamino)-benzoic acid-(2-ethylhexyl)ester; esters of cinnamic acid such as 4-methoxy cinnamic acid (2-ethylhexyl)ester, benzophenone derivatives such as 2-hydroxy-4-methoxy benzophenone.

Preferred oil-soluble UV filters are Butyl-Methoxybenzoylmethane, Ethylhexyl Methoxycinnamate, Ethylhexyl Salicylate, and Bis-Ethyl Hexyl Phenol Methoxyphenyl Triazine.

Water-soluble UVB filters are, for example, sulfonic acid derivatives of benzophenone or of 3-benzylidene camphor or salts, such as Na or K salts, of 2-phenyl benzimidazole-5-sulfonic acid.

UVA filters include dibenzoyl methane derivatives such as Butyl-Methoxybenzoylmethane.

Specially preferred are Butyl Methoxydibenzoylmethane, Ethylhexyl Methoxycinnamate, Ethylhexyl Salicylate, Octocrylene, Ethylhexyl Methoxycinnamate, Isoamyl-p-Methoxycinnamate, Ethylhexyltriazone, Diethylhexyl Butamido Triazone, Methylene Bis-Benzotriazolyl Tetramethylbutylphenol, Disodium Phenyl Dibenzimidazole Tetrasulfonate, Bis-Ethylhexyloxyphenol Methoxyphenyl Triazine, Benzophenone-3. Inorganic pigments as sunscreen filters are metal oxides such as $TiO_2$, $SiO_2$, $Fe_2O_3$, $ZrO_2$, MnO, $Al_2O_3$, which can also be used in mixtures thereof.

Mixtures of the inventive cosmetic compositions together with other tanning agents are possible but not preferred. Such other tanning agents are e.g. isatin, glycerine aldehyde, mesotartaric acid aldehyde, glutaraldehyde, erythrulose, pirazoline-4,5-dion derivatives, dihydroxyacetone (DHA), 4,4-dihydroxy pirazoline-5-dion derivatives.

Compositions with the tanning ingredients of the invention can also comprise humectants such as glycerine, butylene glycol, propylene glycol and mixtures thereof.

Further ingredients for the cosmetics of the present invention are oils, emulsifiers, esters and pigments.

Oils used for the invention can be usual cosmetic oils such as mineral oil, hydrogenated polyisobutene, squalane from synthetic or natural sources, saturated or unsaturated vegetable oils, or mixtures of two or more thereof.

Especially suitable oils are, for example, silicone oils, mineral oils, hydrogenated polyisobutene, polyisoprene, squalane, tridecyltrimellitate, trimethylpropane triisostearate, isodecylcitrate, neopentyl glycol diheptanoate, PPG-15-stearyl ether, calendula oil, jojoba oil, avocado oil, macadamia nut oil, castor oil, cocoa butter, Inca inchi oil, coconut oil, corn oil, cotton seed oil, olive oil, palm kernel oil, rapeseed oil, safflower seed oil, sesame seed oil, soybean oil, sunflower seed oil, wheat germ oil, grape kernel oil, kukui nut oil, thistle oil and mixtures thereof.

Depending upon the oils selected, the cosmetic properties of the solid composition such as softness, hardness or spreading effects are affected.

Suitable esters of polyols are esters of $C_{10}$-$C_{15}$ fatty acids and alcohols, esters of $C_{10}$-$C_{15}$ fatty acids and glycols, or esters of hydroxy fatty acids. Branched $C_{12}$-$C_{15}$ alkyl esters in conjunction with other esters such as di- or tri-esters of polyols are particularly advantageous in the oil phase, with esters of linear-chain alcohols and branched acids being particularly favourable. All these suitable esters are derived from primary alcohols. Preferred esters are Dicaprylyl Carbonate/Decyl Cocoate, Diisopropyl Sebacate/Dibutyl Adipate and Isopropyl Palmitate.

Suitable substances for the oil phase include Neopentyl Glycol Diheptanoate, Propylene Glycol Dicaprylate, Dioctyl Adipate, Coco-Caprylate/Caprate, Diethylhexyl Adipate, Diisopropyl Dimer Dilinoleate, Diisostearyl Dimer Dilinoleate, Butyrospermum Parkii (Shea) Butter, $C_{12-13}$ Alkyl Lactate, Di-$C_{12-13}$ Alkyl Tartrate, Tri-$C_{12-13}$ Alkyl citrate, $C_{12-15}$ Alkyl Lactate, PPG Dioctanoate, Diethylene Glycol Dioctanoate, Meadowfoam Oil, Babassu Oil, Jojoba Oil, Rice Oil, $C_{12-15}$ Alkyl Oleate, Avocado Oil, Tridecyl Neopentanoate, Beeswax, Cetearyl Alcohol and Polysorbate 60, $C_{18-26}$ Triglycerides, Cetearyl Alcohol & Cetearyl Glucoside, Acetylated Lanolin, VP/Eicosene Copolymer, Glyceryl Hydroxystearate, $C_{18-36}$ Acid Glycol Ester, with substances such as $C_{18-36}$ Triglycerides, Glyceryl Hydroxystearate and mixtures thereof. Also suitable and preferred are Cetyl Alcohol & Glyceryl Stearate & PEG 75 Stearate & Ceteth-20 & Steareth-20, Lauryl Glucoside & Polyglyceryl-2 Dipolyhydroxystearate, Beheneth-25, Polyamide-3 & Pentaerythrityl Tetra-Di-T-Butyl Hydroxycinnamate, Polyamide-4 and PEG-100 Stearate, Potassium Cethylphosphate, Stearic Acid and Hectorites.

Cosmetic compositions according to the invention may preferably exist as O/W or W/O emulsions as well as emulsion from the above-mentioned type of multiple, micro or nano emulsions. Suitable emulsifiers for O/W emulsions are for instance addition products of 2-30 mol ethylene oxide to linear $C_8$-$C_{22}$ fatty alcohols, to $C_{12}$-$C_{22}$ fatty acids and to $C_8$-$C_{15}$ alkylphenols; $C_{12}$-$C_{22}$ fatty acid monoesters and diesters of addition products of 1-30 mol ethylene oxide to glycerine; glycerine monoesters and diesters as well as sorbitan monoester and diester of $C_6$-$C_{22}$ fatty acids, polyol- and polyglycerine ester; addition products of ethylene oxide to castor oil; as well as ampholytic tensides.

Suitable emulsifiers for W/O emulsions are for instance addition products of 2-15 mol ethylene oxide to castor oil, esters of $C_{12}$-$C_{22}$ fatty acids and glycerine, polyglycerine, glycols, pentaerythrite, sugar alcohols (e.g. sorbite), polyglucosides (e.g. cellulose), polyalkylene glycols, wool alcohols, copolymers of polysiloxan polyalkyl polyether.

Suitable emulsifiers for multiple emulsions and micro emulsions are for instance Tribehenin PEG-20 Esters, PEG-12 Dimethicone Crosspolymer, Lauryl PEG/PPG-18/18 Methicone, PEG-PPG-19/19 Dimethicone including Cyclopentasiloxane, Polyglyceryl-6 Dioleate and PEG-8 Caprylic/Capric Glycerides.

Pigments, pigment mixtures or powders with a pigment-like effect, also including those with a pearl-gloss effect, may include, for example, iron oxides, aluminium silicates such as ochre, titanium dioxide, mica, kaolin, manganese containing clays, silicium dioxide, zinc oxide, calcium carbonate, French chalk, mica-titanium oxide, mica-titanium oxide-iron oxide, nylon beads, ceramic beads, expanded and non-expanded synthetic polymer powders, powdery natural organic compounds such as milled solid algae, milled plant parts, encapsulated and non-encapsulated cereal starches and mica-titanium oxide-organic dye.

The invention shall now be described in detail by examples. All figures given for the ingredients are % by weight if not specified otherwise.

EXAMPLES

Examples 1 to 3

Tanning Lotions SPF 15

Phase A

|  | Example 1 | Example 2 | Example 3 |
|---|---|---|---|
| Isoamyl P-Methoxycinnamate | 2.0 | 2.0 | 2.0 |
| Ethyl Hexyl Triazone | 1.0 | 1.0 | 1.5 |
| Butyl Methoxydibenzoylmethane | 3.0 | 3.0 | 3.5 |
| Bis-Ethylhexyloxyphenol Methoxyphenyl Triazine | 1.0 | 1.0 | 0.8 |
| Diisopropyl Sebacate | 8.0 | 7,5.0 | 6.5 |
| Cetyl Alcohol & Glyceryl Stearate & PEG-75 Stearate & Ceteth-20 & Steareth-20 | 1.3 | 1.6 | 1.8 |
| Cyclopentasiloxane & Cyclohexasiloxane | 3.5 | 3.2 | 2.8 |
| Hydrogenated Palm Kernel Glycerides & Hydrogenated Palm Glycerides | 0.8 | 1.2 | 0.9 |
| *Mauritia Flexuosa* Fruit Oil | 0.1 | 0.5 | 1.5 |
| Vegetable Oil & Hydrogenated Vegetable Oil & *Euphorbia Cerifera* (Candelilla) Wax | 2.4 | 2.3 | 2.7 |

Phase B

|  | Example 1 | Example 2 | Example 3 |
|---|---|---|---|
| Water | q.s. ad 100 | q.s. ad 100 | q.s. ad 100 |
| Disodium EDTA | 0.09 | 0.06 | 0.08 |
| Sodium Polyacrylate | 0.25 | 0.3 | 0.2 |
| Glycerine | 5.0 | 4.0 | 6.0 |
| Ammonium Acryloyldimethyltaurate/VP Copolymer | 0.15 | 0.3 | 0.5 |
| Caffeine | 0.3 | 0.8 | 0.6 |
| Butylene Glycol | 1.0 | 2.5 | 3.0 |

Phase C

| | Example 1 | Example 2 | Example 3 |
|---|---|---|---|
| Cyclopentasiloxane & Dimethiconol | 2.0 | 2.1 | 2.5 |

Phase D

|  | Example 1 | Example 2 | Example 3 |
|---|---|---|---|
| Plant Extract Mixture[1] of Alcohol & *Coffea Arabica* (Coffee) Seed Extract & *Camellia Sinensis* Leaf Extract & *Pongamia Pinnata* Seed Extract & *Angelica* Root Extract | 0.2 | 0.8 | 0.5 |
| Water | 5 | 6 | 8 |
| Glycine | 0.07 | 0.1 | 0.5 |
| Hydrolyzed *Citrus Aurantium Dulcis* Fruit Extract | 0.03 | 0.2 | 0.07 |
| Sodium Lactate Methylsilanol | 0.25 | 0.02 | 0.3 |
| PEG-8 & Tocopherol & Ascorbyl Palmitate & Citric Acid & Ascorbic Acid | 0.1 | 0.09 | 0.08 |
| Fragrance | 0.25 | 0.2 | 0.4 |
| Alcohol (Ethanol) | 3.0 | 4.5 | 5.5 |

[1]Concentration of plant extracts each 0.2% by weight and ethanol 2-9% by weight related to the total weight of the plant extract mixture.

The ingredients of phase A are mixed and melted together at approximately 75° C. Phase B is heated up to 75° C.

Phase A is added to Phase B and emulsified while stirring, then cooled to 50° C. Phase C is added while stirring. Further cooling while stirring to <30° C.

After that Phase D is added while stirring till homogeneity.

Example 4

Tanning Lotion SPF 30

Phase A

| | |
|---|---|
| Ethylhexyl Palmitate | 3.8 |
| C12-15 Alkyl Benzoate | 8.0 |
| Isopropyl Palmitate | 3.0 |
| Titanium Dioxide/Aluminium Hydroxide/Stearic Acid | 2.0 |
| Butyl Methoxydibenzoylmethane | 2.0 |
| Octyl Methoxycinnamate | 0.5 |
| Bis-Ethylhexyloxyphenol Methoxyphenyl Triazine | 2.0 |
| Octocrylene | 2.0 |
| Diethylhexyl Butamido Triazone | 2.5 |
| Stearic Acid | 2.1 |
| Tribehenin PEG-20 Esters | 2.9 |
| *Zea Mays* (Corn) Oil & Beta Carotene | 0.01 |

Phase B

| | |
|---|---|
| Deionised Water | ad q.s. |
| Disodium EDTA | 0.05 |
| Caffeine | 0.8 |
| Glycerine | 8.0 |
| Propylene Glycol | 3.0 |
| Hydroxypropyl Methylcellulose | 0.35 |
| Acrylates/C10-30 Alkyl Acrylate Crosspolymer | 0.2 |
| Potassium Cetyl Phosphate | 0.5 |
| Phenoxyethanol | 0.7 |
| Chlorphenesin | 0.2 |

Phase C

| | |
|---|---|
| Cyclopentasiloxane | 5.0 |

Phase D

| | |
|---|---|
| Methylene Bis-Benzotriazolyl Tetramethylbutylphenol/Water/Decyl Glucoside/Propylene Glycol/Xanthan Gum | 4.0 |
| *Elaeis Guineensis* (Palm) Oil | 0.15 |
| *Bixa Orellana* Seed Extract | 0.175 |
| *Mauritia Flexuosa* Fruit Oil | 1.3 |
| Glycine | 0.1 |
| Sodium Lactate Methylsilanol | 0.25 |
| Hydrolysed *Citrus Aurantium Dulcis* Fruit Extract | 1.0 |
| Alcohol/*Coffea Arabica* (Coffee) Seed Extract *Camellia Sinensis* Leaf Extract/*Pongamia Pinnata* Seed Extract/*Angelica Archangelica* Root Extract | |
| Triethanolamine | 0.3 |

Process

Phase A is heated up to 75° C., Phase B is heated separately. Phase A and Phase B are then emulsified while stirring at 75° C. Cooling down while stirring to 50-55° C. Adding of Phase C while stirring till homogeneity and 2$^{nd}$ cooling to <30° C. Adding of Phase D with final stirring and homogenising.

Example 5

After Sun Gel

Phase A

| | |
|---|---|
| Deionised Water | q.s. ad 100 |
| EDTA | 0.04 |
| Allantoin | 0.1 |
| Caffeine | 1.2 |
| Xanthan Gum | 0.1 |
| Glycerine | 4.0 |
| Propylene Glycol | 3.0 |
| Magnesium Aluminium Silicate | 0.1 |
| Acrylates/C10-30 Alkyl Acrylates Crosspolymer | 0.7 |

Phase B

| | |
|---|---|
| Triethanolamine | ad q.s. to pH 5.5 |
| Glycine | 0.08 |
| Hydrolysed *Citrus Aurantium Dulcis* Fruit Extract | 0.07 |
| Sodium Lactate Methylsilanol | 0.25 |
| *Mauritia Flexuosa* Fruit Oil | 0.5 |
| *Bixa Orellana* Seed Extract | 0.1 |
| Caprylic/Capric Triglyceride | 1.8 |
| *Elaeis Guineensis* Palm Oil | 0.1 |
| *Zea Mays* (Corn) Oil & Beta Carotene | 0.01 |
| PEG-40 Hydrogenated Castor Oil | 1.0 |

Phase C

| | |
|---|---|
| Phenoxyethanol | 0.5 |
| 1,2 Hexanediol/Caprylyl Glycol | 0.3 |
| Alcohol | 5.0 |

Process

Heat Phase A water to 45° C. while stirring till homogeneity. Continue while stirring with adding of ingredients of Phase B to Phase A, first the neutralisation. Cooling to 30° C. while stirring. Finalisation by adding Phase C while stirring till homogeneity. Adjust pH to 5.5.

Example 6

Dermatological Tanning Ointment (Pre-Sun)

Phase A

| | |
|---|---|
| Steareth-2 (Macrogolstearylether) | 2.7 |
| Steareth-21 | 1.7 |
| Isopropyl Myristate | 4.0 |
| Cetostearylisononanoate | 5.0 |
| Triglycerides | 2.0 |
| *Butyrospermum Parkii* (Shea) Butter | 1.5 |
| Petrolatum | 5.0 |

Phase B

| | |
|---|---|
| Deionised Water | q.s. ad 100 |
| Propylene Glycol | 2.0 |
| EDTA | 0.03 |

-continued

| Caffeine | 0.2 |
| Carbomer Interpolymer Type B | 0.2 |
| Glycerol 99% | 4.0 |
| Magnesium Aluminium Silicate | 0.4 |
| Xanthan Gum | 0.4 |

Phase C

| Cyclomethicone NF | 3.0 |
| Panthenol | 1.5 |

Phase D

| Jojoba Oil | 2.0 |
| DL alpha Tocopheryl Acetate | 0.3 |
| *Mauritia Flexuosa* Fruit Oil | 3.0 |
| Zea Mays (Corn) Oil & Beta Carotene | 0.01 |
| Bixa Orellana Seed Extract | 0.15 |
| *Elaeis Guineensis* Palm Oil | 0.3 |
| Deionised Water | 3.0 |
| Glycine | 0.05 |
| Hydrolysed *Citrus Aurantium Dulcis* Fruit Extract | 0.1 |
| Sodium Lactate Methylsilanol | 0.2 |
| Bronopol | 0.1 |
| Deionised Water | q.s. |
| Sodiumhydroxide (20%) for pH adjustment | ad q.s. pH 5.5 |

Process

The ingredients of Phase A are mixed and heated up to 75° C. Phase B is heated up to 75° C. while stirring till homogeneity. Adding of Phase A to Phase B while stirring till homogeneity at 75° C. Continue stirring and cooling to 50° C. Adding homogenously of Phase C to the emulsion, 2nd cooling to 30° C.

Phase D is added to the emulsion while stirring till homogeneity.

Adjustment of pH to 5.5.

Example 7

Comparative Test

Normal human melanocytes diluted in a MGM-4 culture (MGM=Melanocyte Growth Medium) were treated with the active ingredients of the tanning composition for 8 days. During this period, cells were exposed to six independent UVB radiations, one each day (day 1, day 2, day 3, day 4, day 7, day 8). For that, cells were rinsed with PBS and exposed to UVB of 40 mJ/cm$^2$ for 40 sec. Immediately after irradiation, PBS was removed and replaced by fresh medium containing active ingredients.

24 hours after the last UV exposure, the intracellular melanin content was quantified. Medium was removed, cells were washed with PBS and melanin was extracted by using NaOH-DMSO solution. Melanin extracts were heated at 80° C. during 2 hours. Then, extracts were transferred into a 96-well microplate and the optical densities were measured at 405 nm by using a spectrophotometer. A standard curve of synthetic melanin was performed in the same conditions.

A second plate treated and exposed to UVB in the same conditions was used to determine cells numbers by using the neutral red method. Cells were rinsed with PBS and incubated with neutral red solution for three hours. Then dye was removed and acetic acid-ethanol solution was added to make soluble the intracellular neutral red. Then, solutions were transferred into a 96-well microplate and the optical densities were measured at 540 nm by using a spectrophotometer. A standard curve was performed in the same conditions with known quantities of melanocytes. The intracellular melanin content was normalized with the cells number, and tanning was expressed by comparing melanin content of melanocytes treated with the active ingredients to cells exposed to UVB but without any ingredient.

The results are shown in Table 1.

TABLE 1

| Active ingredient | Tanning (%) |
|---|---|
| (1) Caffeine (0.003%) + glycine (0.0005%) + Sodium Lactate Methylsilanol 0.005 + Copper gluconate (0.00013%) [EP 0380335] | 20 |
| (2) Caffeine (0.5%) + glycine (0.05%) + Sodium Lactate Methylsilanol (0.1%) | 12 |
| (3) Hydrolyzed *Citrus auranthium dulcis* Fruit Extract (0.02%) | 27 |
| (4) *Mauritia Flexuosa* Fruit Oil (0.1%) | 205 |
| (5) Caffeine (0.05%) + glycine (0.005%) + Sodium Lactate Methylsilanol (0.099%) + Hydrolysed *Citrus Auranthium Dulcis* Fruit Extract (0.02%) + *Mauritia Flexuosa* Fruit Oil (0.1%) (Tanning ingredients of the invention) | 300 |

The result shows that the sum of the individual tanning effects (12+27+205=244%) is remarkably lower than the 300% of the tanning composition of the invention.

The invention claimed is:

1. A cosmetic composition for use in tanning human skin consisting of:
    0.05 to 2.0% Caffeine,
    0.01 to 1.0% Glycine,
    0.001 to 0.2% Hydrolyzed Citrus Aurantium Dulcis Fruit Extract; 0.05 to 0.5% Sodium Lactate Methylsilanol and 0.05 to 3.0% Mauritia Flexuosa Fruit Oil and
    up to 100% of dermatological or cosmetic auxiliaries selected from the group consisting of: water, vitamins, a mixture of the plant extract of Angelica Archangelica Root Extract, Camellia Sinensis Leaf Extract, Pongamia Pinnata Seed Extract and Coffee Arabica Seed Extract, synthetic polymers, esters, ethers, fatty acids, monovalent and multivalent alcohols, silicones and silicates;
    all percentages being % by weight and related to the total weight of the cosmetic composition.

2. The cosmetic composition according to claim 1, wherein the cosmetic composition additionally comprises Red Palm (Elaeis Guineensis) Oil, Bixa Orellana Seed Extract or mixtures thereof.

3. The cosmetic composition according to claim 1, wherein the amount of Caffeine is 0.1 to 1.2% by weight.

4. The cosmetic composition according to claim 1, wherein the amount of Hydrolyzed Citrus Aurantium Dulcis Fruit Extract is 0.01 to 0.05% by weight.

5. The cosmetic composition according to claim 1, wherein the amount of Mauritia Flexuosa Fruit Oil is 0.05 to 1.0% by weight.

6. The cosmetic composition according to claim 1, wherein the amount of Sodium Lactate Methylsilanol is 0.02 to 0.25% by weight.

7. The cosmetic composition according to claim 2, wherein the amount of Red Palm Oil is 0.05 to 1.5% by weight.

8. The cosmetic composition according to claim 2, wherein the amount of Bixa Orellana Seed Extract is 0.005 to 0.5% by weight.

9. The cosmetic composition according to claim 1, wherein the cosmetic composition is a lotion, oil, cream, gel, mask, balm, powder, tan glow, pre-sun product, sun product, after-sun product, self-tan, make-up, compact powder, photoprotecting product or, spray.

10. A method for tanning human skin by applying to skin areas in need of tanning a cosmetic composition consisting of:
- 0.05 to 2.0% Caffeine,
- 0.01 to 1.0% Glycine,
- 0.001 to 0.2% Hydrolyzed Citrus Aurantium Dulcis Fruit Extract;
- 0.05 to 0.5 Sodium Lactate Methylsilanol and
- 0.05 to 3.0% Mauritia Flexuosa Fruit Oil; and
- up to 100% of dermatological or cosmetic auxiliaries, selected from the group consisting of: water, vitamins, a mixture of the plant extract of Angelica Archangelica Root Extract, Camellia Sinensis Leaf Extract, Pongamia Pinnata Seed Extract and Coffee Arabica Seed Extract, synthetic polymers, esters, ethers, fatty acids, monovalent and multivalent alcohols, silicones and silicates;
- all percentages being % by weight and related to the total weight of the cosmetic composition.

* * * * *